US012569562B2

(12) United States Patent (10) Patent No.: US 12,569,562 B2
Shiku et al. (45) Date of Patent: Mar. 10, 2026

(54) PRETREATMENT DRUG FOR T CELL INFUSION THERAPY FOR IMMUNE-CHECKPOINT INHIBITOR-RESISTANT TUMOR

(71) Applicants: MIE UNIVERSITY, Tsu (JP); KYOTO UNIVERSITY, Kyoto (JP)

(72) Inventors: Hiroshi Shiku, Tsu (JP); Naozumi Harada, Tsu (JP); Daisuke Muraoka, Tsu (JP); Kazunari Akiyoshi, Kyoto (JP)

(73) Assignees: MIE UNIVERSITY, Tsu (JP); KYOTO UNIVERSITY, Kyoto (JP)

( * ) Notice: Subject to any disclaimer, the term of this patent is extended or adjusted under 35 U.S.C. 154(b) by 692 days.

(21) Appl. No.: 18/071,010

(22) Filed: Nov. 29, 2022

(65) Prior Publication Data

US 2023/0201263 A1 Jun. 29, 2023

Related U.S. Application Data

(62) Division of application No. 16/077,238, filed as application No. PCT/JP2017/004552 on Feb. 8, 2017, now abandoned.

(30) Foreign Application Priority Data

Feb. 8, 2016 (JP) ................................. 2016-022081

(51) Int. Cl.
| | |
|---|---|
| *A61K 47/36* | (2006.01) |
| *A01K 67/027* | (2024.01) |
| *A61K 9/14* | (2006.01) |
| *A61K 39/00* | (2006.01) |
| *A61K 40/11* | (2025.01) |
| *A61K 40/32* | (2025.01) |
| *A61K 40/42* | (2025.01) |
| *A61K 45/00* | (2006.01) |
| *C07K 14/00* | (2006.01) |

(52) U.S. Cl.
CPC ............ *A61K 47/36* (2013.01); *A01K 67/027* (2013.01); *A61K 9/14* (2013.01); *A61K 40/11* (2025.01); *A61K 40/32* (2025.01); *A61K 40/4251* (2025.01); *A61K 45/00* (2013.01); *C07K 14/00* (2013.01); *A61K 39/00* (2013.01); *A61K 2239/31* (2023.05)

(58) Field of Classification Search
None
See application file for complete search history.

(56) References Cited

U.S. PATENT DOCUMENTS

| | | | | |
|---|---|---|---|---|
| 5,731,160 A | * | 3/1998 | Melief ................. | C12N 5/0636 |
| | | | | 435/375 |
| 6,656,481 B1 | | 12/2003 | Shiku et al. | |

| | | | | |
|---|---|---|---|---|
| 7,202,034 B2 | * | 4/2007 | Van Der Burg ....... | A61K 39/12 |
| | | | | 435/6.14 |
| 8,158,131 B2 | | 4/2012 | Apt et al. | |
| 9,243,227 B2 | | 1/2016 | Shiku et al. | |
| 9,422,356 B2 | | 8/2016 | Lee et al. | |
| 9,603,874 B2 | | 3/2017 | Shiku et al. | |
| 2004/0198684 A1 | | 10/2004 | Shiku | |
| 2006/0183669 A1 | | 8/2006 | Hansen et al. | |
| 2008/0166369 A1 | | 7/2008 | Shiku et al. | |
| 2008/0187535 A1 | | 8/2008 | Blais et al. | |
| 2009/0246213 A1 | | 10/2009 | Shiku | |
| 2010/0029912 A1 | | 2/2010 | Blais et al. | |
| 2010/0062011 A1 | | 3/2010 | Yano | |
| 2012/0029175 A1 | | 2/2012 | Nagura et al. | |
| 2014/0112956 A1 | | 4/2014 | Karlsson-Parra et al. | |
| 2014/0322344 A1 | * | 10/2014 | Shiku .................. | A61K 39/385 |
| | | | | 424/193.1 |
| 2016/0367651 A1 | | 12/2016 | Shiku et al. | |

(Continued)

FOREIGN PATENT DOCUMENTS

| | | |
|---|---|---|
| CN | 103502439 A | 1/2014 |
| CN | 103957930 A | 7/2014 |

(Continued)

OTHER PUBLICATIONS

Ly, Long V., et al. "Peptide vaccination after T-cell transfer causes massive clonal expansion, tumor eradication, and manageable cytokine storm." Cancer research 70.21 (2010): 8339-8346. (Year: 2010).*
Muraoka, Daisuke, et al. "Nanogel-based immunologically stealth vaccine targets macrophages in the medulla of lymph node and induces potent antitumor immunity." ACS nano 8.9 (2014): 9209-9218 and S1-S11. (Year: 2014).*
Maus, Marcela V., et al. "Adoptive immunotherapy for cancer or viruses." Annual review of immunology 32.1 (2014): 189-225. (Year: 2014).*
Rosenberg, Steven A., and Nicholas P. Restifo. "Adoptive cell transfer as personalized immunotherapy for human cancer." Science 348.6230 (2015): 62-68. (Year: 2015).*
Partial European Search Report from the European Patent Office dated May 2, 2017 in related EP application No. 14850811.2, including European Search Opinion, Supplemental Partial European Search Report, and examined claims 1-9.

(Continued)

*Primary Examiner* — Bethany P Barham
*Assistant Examiner* — Peter Anthopolos
(74) *Attorney, Agent, or Firm* — J-TEK LAW PLLC; Jeffrey D. Tekanic; Scott T. Wakeman

(57) ABSTRACT
An antigen-loaded nanogel is formed by loading or encapsulating one or more long peptide antigens or one or more protein antigens in a hydrophobized polysaccharide. The long peptide antigen(s) or protein antigen(s) contains (or each contain) one or more CD8+ cytotoxic T cell recognition epitopes and/or one or more CD4+ helper T cell recognition epitopes, which is/are derived from the antigen. The antigen-loaded nanogel is administered at least one day prior to administration of antigen-specific T cells to improve the efficacy of a T cell infusion therapy against an immune checkpoint inhibitor-resistant tumor. The hydrophobized polysaccharide may be pullulan having cholesteryl groups bound thereto. An immune-enhancing agent also may be administered in or with the antigen-loaded nanogel.

20 Claims, 6 Drawing Sheets

Specification includes a Sequence Listing.

(56) References Cited

U.S. PATENT DOCUMENTS

| | | |
|---|---|---|
| 2017/0035870 A1 | 2/2017 | Karlsson-Parra et al. |
| 2017/0266079 A1 | 9/2017 | Hanotin et al. |
| 2017/0267783 A1 | 9/2017 | Nezu et al. |
| 2018/0177816 A1 | 6/2018 | Shiku et al. |

FOREIGN PATENT DOCUMENTS

| | | |
|---|---|---|
| EP | 1428879 A | 6/2004 |
| EP | 1579870 A | 9/2005 |
| EP | 1834650 A1 | 9/2007 |
| EP | 2006302 A2 | 12/2008 |
| JP | S6169801 A | 4/1986 |
| JP | H03292301 A | 12/1991 |
| JP | H0797333 A | 4/1995 |
| JP | 2002255995 A | 9/2002 |
| JP | 4033497 B2 | 1/2008 |
| WO | 2001057182 A2 | 8/2001 |
| WO | 2006077724 A1 | 7/2006 |
| WO | 2007097251 A1 | 8/2007 |
| WO | 2007119859 A1 | 10/2007 |
| WO | 2008089074 A | 7/2008 |
| WO | 2011090065 A1 | 7/2011 |
| WO | 2013031882 A1 | 3/2013 |
| WO | 2015050158 A1 | 4/2015 |

OTHER PUBLICATIONS

Prehn, Cancer Cell Int., 2005; vol. 5 (1): 25; pp. 1-6.
Ribas, A et al. J. Clin. Oncol. 2003; vol. 21(12): pp. 2415-2432.
Bette et al., Tissue Antigens. 2002: vol. 59, Abstract.
Shariat et al., Iran J. Basic Med. Sci., 2015; vol. 18 (5): pp. 506-513.
Shen, et al., Curr. Opin. Immunol. 2006; vol. 18(1): pp. 85-91.
Shiku H., "Multicenter clinical study of multivalent cancer vaccine with new antigen protein delivery system", Ministry of Education, Culture, Sports, Science and Technology, Gan TR Jigyo 3 Kai Gan Seika Hokokukai Shorokushu, published at http://www.ctrp.mext.go.jp/pdf/3rd/3rd_abreport_04_shiku.pdf, Mar. 3, 2007, including English abstract attached thereto.
Shiku, H. Int. J. Hematol. 2003; vol. 77(5): pp. 435-438.
Shimizu, Takeshi et al., "Nanogel DDS enables sustained release of IL-12 for tumor immunotherapy", Biochemical and Bioph. Res. Communications, vol. 367, No. 2, pp. 330-335, 2007, doi: 10.1016/J.BBRC.2007.12.112.
Shimoda, Asako et al.,: "Dual crosslinked hydrogel nanoparticles by nanogel bottom-up method for sustained-release delivery", Colloids and Surfaces B: Biointerfaces, vol. 99 , pp. 38-44, 2012, doi: 10.1016/J.COLSURFB.2011.09.025.
Slinghuff et al., Cancer Immunol. Immunother., 2000; vol. 48 (12), Abstract.
Takahashi, N., et al., "First clinical trial of cancer vaccine therapy with artificially synthesized helper/killer-hybrid epitope long peptide of MAGE-A4 cancer antigen", Cancer Sci., 2012, vol. 103(I), pp. 150-153.
Tsuji, T., et al., Antibody-Targeted NY-ESO-1 to Mannose Receptor or DEC-205 In Vitro Elicits Dual Human CD8+ and CD4+ T Cell Responses with Broad Antigen Specificity, J Immunol 2011; vol. 186, pp. 1218-1227; Prepublished online Dec. 13, 2010.
Tumeh, P. C., et al. Nature. 2014; vol. 515(7528) :pp. 568-571.
Uenaka, A et al., "T cell immunomonitoring and tumor responses in patients immunized with a complex of cholesterol-bearing hydrophobized pullulan (CHP) and NY-ESO-1 protein", Cancer Immunity, 2007, vol. 7, p. 9-20.
Van der Burg, S, et al., Vaccines for established cancer: overcoming the challenges posed by immune evasion, Nature Reviews / Cancer, 2016, vol. 16: pp. 219-233, published online Mar. 11, 2016.
Wang et al., Scand. J. Immunol. 2004; vol. 60 (3): pp. 219-225.
Zamarin, D., et al., Sci. Transl. Med., 2014; vol. 6(226): p. 226ra32, pp. 1-20.
Akiyoshi, K., et al., J. Proc. Japan. Acad., 1995; vol. 71(71B): pp. 15-19.

Akiyoshi, K., et al., Macromolecules., 1993; vol. 26(12): pp. 3062-3068.
Australian Office Action dispatched Jul. 5, 2021, in related AU application No. 2017216653.
Behrens, G. et al., Immunol. Cell Biol. 2004; vol. 82(1): pp. 84-90.
Bergmann C et al. "Flanking Residues Alter Antigenicity and Immunogenicity of Multi-Unit CTL Epitopes", The Journal of Immunology, the American Association of Immunologists, vol. 157, No. 8, Jan. 1996, pp. 3242-3249.
Brewer, J. M., et al., J. Immunol. 1998; vol. 161: pp. 4000-4007.
Byrd-Leifer, C. A., et al., Eur. J. Immunol., 2001; vol. 31(8): pp. 2448-2457.
Chinese Office Action dispatched Apr. 30, 2021, in related CN application No. 201780010486.9, and machine translation thereof.
Chinese Office Action dispatched Oct. 22, 2021, in related CN application No. 201780010486.9, and machine translation thereof.
Chinese Search Report dated Apr. 14, 2021, in related CN application No. 201780010486.9.
Communication issued Sep. 30, 2020 in related EP application No. 17 750 278.8, including European Office Action and examined claims 1-8.
Ohtake, J., et al., "Identification of novel helper epitope peptides of Survivin cancer associated antigen applicable to developing helper/ killer-hybrid epitope long peptide cancer vaccine", Immunol. Lett., 2014; vol. 161(I), Abstract.
Depla et al., J. Virol. 2008; vol. 82: pp. 435-450.
Dhodapkar, M., et al., Induction of Antigen-Specific Immunity with a Vaccine Targeting NY-ESO-1 to the Dendritic Cell Receptor DEC-205, Science Translational Medicine 6 (232), 232ra51 1-9, published Apr. 16, 2014.
English translation of International Preliminary Report on Patentability dated Jun. 7, 2018 for parent application No. PCT/JP2017/004552.
English translation of the International Search Report dated Mar. 28, 2017 for parent application No. PCT/JP2017/004552.
Extended European Search Report issued Nov. 12, 2019 in related EP application No. 17 750 278.8, including European Search Opinion, Supplementary European Search Report and examined claims 1-13.
Finn, O., The dawn of vaccines for cancer prevention, Nature Reviews / Immunology, doi:10.1038/ hri.2017.140, published online Dec. 27, 2017.
Fu, J., et al. Sci. Transl. Med. 2015; vol. 7(283):283ra52, pp. 1-24.
Gallou et al., Oncotarget. Sep. 13 2016; vol. 7 (37): pp. 59417-59428.
Goldberg, A. L., et al., Mol. Immunol. 2002; vol. 39(3-4): pp. 147-164.
Gu, X. G., et al., Cancer Res., 1998; vol. 58(15): pp. 3385-3390.
Hasegawa, K., et al., Clin. Cancer Res., 2006; vol. 12(6): pp. 1921-1927.
Henriksen-Lacey, M., et al., J. Controlled Release. 2011; vol. 154(2): pp. 131-137.
Holland, C. J., et al., Front Immunol. 2013; vol. 4: Article 172, pp. 1-9.
Kuta et al., Blood. 2002; vol. 99 (10): pp. 3717-3724.
Japanese Office Action dispatched Sep. 2, 2020, in related JP application No. 2017-566975, and machine translation thereof.
John, L. B., et al., Clin. Cancer Res. 2013; vol. 19(20): pp. 5636-5646.
June, Carl H., "Adoptive T cell therapy for cancer in the clinic", Journal of Clinical Investigation, vol. 117, No. 6, pp. 1466-1476, Jun. 2007, doi: 10.1172/JCI32446.
Kageyama, S., et al., Dose-dependent effects of NY-ESo-1 protein vaccine complexed with cholesteryl pullulan (CHP-NY-ESo-1) on immune responses and survival benefits of esophageal cancer patients, J. Translational Medicine, 2013, vol. 11, No. 246, pp. 1-10.
Kakimi, et al., "A phase I study of vaccination with NY-ESO-1f peptide mixed with Picibanil OK-432 and Montanide SA-51 in patients with cancers expressing the NY-ESO-1 antigen", International Journal of Cancer, vol. 129, No. 12, Dec. 2011, pp. 2836-2846.
Kim, K., et al., Proc. Natl. Acad. Sci. U. S. A. 2014; vol. 111(32): pp. 11774-11779.

(56)             References Cited

OTHER PUBLICATIONS

Kitano et al., Clin Cancer Res, 2006; vol. 12(24): pp. 7397-7405.
Kollessery, G., et al., "Tumor-specific peptide based vaccines containing the conformationally biased, response- selective C5a agonists EP54 and EP67 protect against large B cell lymphoma in a syngeneic murine model", Vaccine, 2011, vol. 29, No. 35, doi 10.1016, Abstract.
Kong, L. Y., et al., Clin. Cancer Res. 2008; vol. 14(18): pp. 5759-5768.
Kwon et al., Biochim. Biophys. Acta., 1998; vol. 1388, Abstract.
Livingston et al., J. Immunol. 2002; vol. 168, Abstract.
Masuko, K., et al., "Artificially synthesized helper/killer-hybrid epitope long peptide (H/K-Help): Preparation and Immunological analysis of vaccine efficacy", Immunol. Lett., vol. 163, No. I, pp. 102-112, [online], Dec. 3, 2014.
Melief, et al., "Effective therapeutic anticancer vaccines based on precision guiding of cytolytic T lymphocytes", Immunological Reviews, 2002; vol. 188, pp. 177-182.

Melief, et al., Nature Rev. Cancer, 2008; vol. 8(5): pp. 351-360.
Muraoka, D., et al., J. Immunol. 2010; vol. 185(6): pp. 3768-3776.
Muraoka, D., et al., Vaccine. 2013; vol. 31: pp. 2110-2118.
Muraoka, et al., "Nanogel-Based Immunologically Stealth Vaccine Targets Macrophages in the Medulla of Lymph Node and Induces Potent Antitumor Immunity", ACS Nano, vol. 8, No. 9, Sep. 2014; pp. 9209-9218.
Nakanishi, T., et al., J. Controlled Release. 1999; vol. 61: pp. 233-240.
Naoko Imai et al., "Tokushu: Kokei Gan no Men'eki-Kotai Ryoho, III. Rinsho Oyo no Shinpo to Tenbo Men'eki Ryoho" (Targeting cancer antigen (MAGE-A4, NY-ESO-1) for immunotherapy), Japanese Journal of Clinical Medicine, 2012, vol. 70, No. 12, pp. 2125-2129.
Nezafat, N., et al., "A novel multi-epitope peptide vaccine against cancer: an in silico approach", J. Theor. Biol., 2014; vol. 349, Abstract.
Nishikawa, T., et al., Macromolecules. 1994; vol. 27(26): pp. 7654-7659.

* cited by examiner

CD8-positive T cells (%, per CD45-positive cells)

Fig. 3(A)

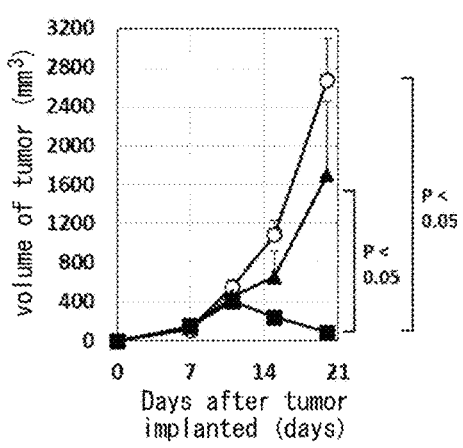

○ untreated group

■ pretreatment drug (long peptide antigen loaded CHP nanogel + CpG oligo DNA, subcutaneous administration) + antigen-specific T cell infusion ▲ pretreatment drug (long peptide: IFA mixed + CpG oligo DNA, subcutaneous administration) + antigen-specific T cell infusion

Fig. 3(B)

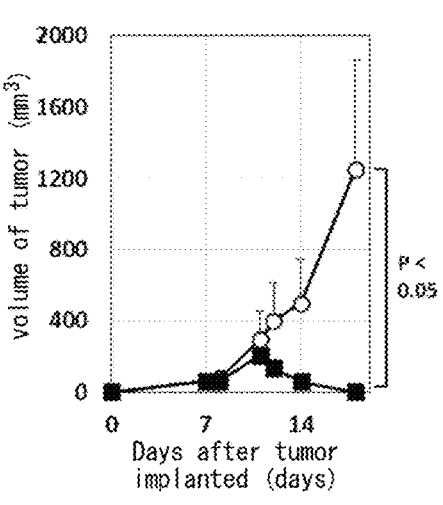

○ untreated group

■ pretreatment drug (long peptide antigen loaded CHP nanogel + CpG oligo DNA, intravenous administration) + antigen-specific T cell infusion

Fig. 3(C)

○ untreated group

■ pretreatment drug (long peptide antigen loaded CHP nanogel + Poly-IC RNA, intravenous administration) + antigen-specific T cell infusion ▲ pretreatment drug (long peptide antigen loaded CHP nanogel + CpG oligo DNA, intravenous administration) + antigen-specific T cell infusion

Fig. 4(A)

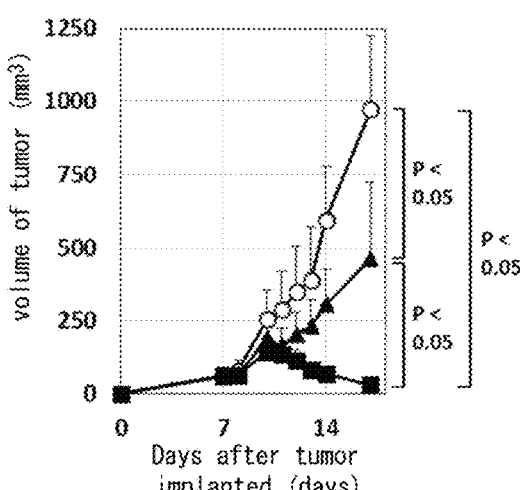

○ untreated group

■ pretreatment drug (long peptide antigen loaded CHP nanogel + CpG oligo DNA, intravenous administration) + antigen-specific T cell infusion ▲ pretreatment agent (only CpG oligo DNA, intravenous administration) + antigen-specific T cell infusion

Fig. 4(B)

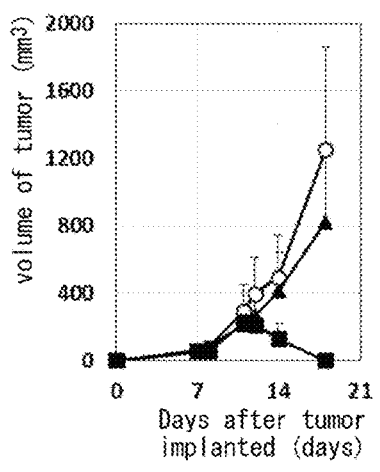

○ untreated group

■ pretreatment drug (long peptide antigen loaded CHP nanogel + CpG oligo DNA, intravenous administration) + antigen-specific T cell infusion ▲ pretreatment drug (only long peptide antigen loaded CHP nanogel, intravenous administration) + antigen-specific T cell infusion

Fig. 4(C)

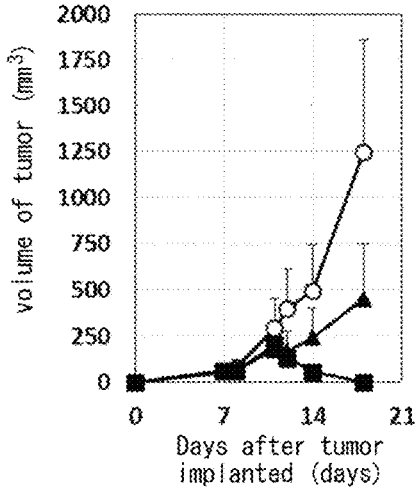

○ untreated group

■ pretreatment drug (long peptide antigen loaded CHP nanogel + CpG oligo DNA, intravenous administration) + antigen-specific T cell infusion ▲ only pretreatment drug (long peptide antigen loaded CHP nanogel + CpG oligo DNA, intravenous administration)

PRETREATMENT DRUG FOR T CELL INFUSION THERAPY FOR IMMUNE-CHECKPOINT INHIBITOR-RESISTANT TUMOR

CROSS-REFERENCE

This application is a divisional application of U.S. patent application Ser. No. 16/077,238, now abandoned, which was the US national stage of International Patent Application No. PCT/JP2017/004552 filed on Feb. 8, 2017, which claims priority to Japanese Patent Application 2016-022081 filed on Feb. 8, 2016.

REFERENCE TO SEQUENCE LISTING FILED VIA EFS-WEB

The present application contains a Sequence Listing that has been electronically submitted in ASCII text format via EFS-Web and is incorporated herein by reference in its entirety. The sequence listing is identified on the electronically-filed text file as follows:

| File Name | Date of Creation | Size (KB) |
|---|---|---|
| MIE007_SEQ_Listing.xml | Nov. 29, 2022 | 5 |

TECHNICAL FIELD

The invention relates to a pretreatment drug that enhances the efficacy of T cell infusion therapy against immune checkpoint inhibitor-resistant tumors.

BACKGROUND ART

T cells play important roles in tumor immune response. T cells recognize antigen protein-derived epitope peptides bound to major histocompatibility complex (MHC) presented on the surface of antigen presenting cells (dendritic cells, macrophages, etc.) through T cell receptors (TCR) expressed on the surface of the T cells. The reaction is called antigen stimulation. Simultaneously with antigen stimulation, co-stimulatory signals are generated by binding between membrane protein CD28 on the T cells and membrane protein CD80 or CD86 on the antigen presenting cells. T cells are appropriately activated by TCR signals via antigen stimulation and by co-stimulatory signals.

In opposition thereto, a regulatory mechanism called immune checkpoint is provided for preventing T cell activity from becoming excessive. Membrane protein CTLA-4 is expressed on activated T cells and binds to CD80 or CD86 on antigen presenting cells. As a result, the binding inhibits the binding of CD28 and CD80, or CD28 and CD86, and prevents the generation of co-stimulatory signals, and inputs inhibitory signals to T cells. CTLA-4 expressed on regulatory T cells binds to CD80 or CD86 on antigen presenting cells, and thereby suppresses the activity of antigen presenting cells. Through these activities, CTLA-4 acts as an immune checkpoint molecule to suppress the activity of T cells.

Membrane protein PD-1 upregulated by activation of T cells is one type of immune checkpoint molecule. PD-L1 is known as a ligand that binds to PD-1. PD-L1 is expressed on many tumor cells and on activated immune cells. When PD-L1 binds to PD-1 on T cells, TCR signals at the time of antigen stimulation are inhibited by PD-1 signals. As a result, cytokine production and the cytotoxicity of T cells are reduced. PD-1 signals may inhibit the proliferation and survival of T cells.

Immune checkpoint molecules such as CTLA-4, PD-1 and PD-L1 weaken the activity of tumor-specific T cells. As a result, these molecules are one of the main causes for tumors to evade immune responses. By inhibiting the action of CTLA-4, PD-1 or PD-L1, the activity of tumor-specific T cells can be recovered, and an immune attack against the tumor can be enhanced. The use of inhibitors of immune checkpoint molecules has been evaluated in a variety of human cancers. CTLA-4 inhibitory antibody and PD-1 inhibitory antibody show superior therapeutic effects, such as tumor regression and prolonged survival, in refractory melanoma, lung cancer and renal cell carcinoma patients. However, the response rate is only 20 to 30 percent in any of the cancer types. Many cancer patients are resistant to immune checkpoint inhibitors. Development of effective treatments for cancer patients who are resistant to immune checkpoint inhibitors has become an important issue in cancer treatment.

Some candidates for the effective treatment of immune checkpoint inhibitor-resistant tumors have been found using in vivo testing systems. A combination therapy of intratumoral administration of an oncolytic virus (Newcastle disease virus) and an anti-CTLA-4 antibody shows a therapeutic effect in a nonclinical tumor model in which a mouse melanoma cell line B16F10, mouse prostate cancer cell line TRAMP-C2, or mouse colon cancer cell line CT26 is implanted subcutaneously into wild type mice. Under these conditions, the anti-CTLA-4 antibody alone does not exhibit any therapeutic effect (non-Patent Document 1). A combination therapy of a tumor cell vaccine transduced with a GM-CSF gene and treated with radiation and a STING agonist and an anti-PD-1 antibody shows a therapeutic effect in a nonclinical tumor model in which a mouse melanoma cell line B16F10 or mouse colon cancer cell line CT26 is implanted subcutaneously into wild type mice. Under these conditions, the anti-PD-1 antibody does not exhibit any therapeutic effect (non-Patent Document 2). A combination therapy of 4 drugs, which include a DNA methylation inhibitor, a HDAC inhibitor, an anti-CTLA-4 antibody, and an anti-PD-1 antibody, shows a therapeutic effect in a nonclinical tumor model in which a mouse breast cancer cell line 4T1 is implanted subcutaneously into wild type mice. Under these conditions, a combination therapy of the anti-CTLA-4 antibody and the anti-PD-1 antibody does not exhibit any therapeutic effect (non-Patent Document 3). A combination therapy of a human Her2-specific chimeric antigen receptor (CAR)-engineered T cell infusion and an anti-PD-1 antibody shows a therapeutic effect in a nonclinical tumor model in which a murine sarcoma cell line 24JK expressing human Her2 antigen is implanted subcutaneously into a human Her2 transgenic mice. Under these conditions, the anti-PD-1 antibody alone does not exhibit any therapeutic effect (non-Patent Document 4).

These reports are characterized by combining immune checkpoint inhibitors and other anti-cancer agents. Therapeutic effects on tumor are observed only in animal tumor models that express molecular targets of immune checkpoint inhibitors.

In human cancers, mechanisms of resistance to immune checkpoint inhibitors have been elucidated. An analysis of tumor tissues of melanoma patients, who exhibit sensitivity or resistance to anti-PD-1 antibody, showed that the expression of PD-L1 and PD-1 in tumors was significantly lower in patients with resistance (non-Patent Document 5). The results indicate that the lack of expression of molecular targets of immune checkpoint inhibitors at the tumor site is a cause of the resistance to the inhibitors. Treatment methods shown in non-Patent Documents 1 to 4 are characterized by combining immune checkpoint inhibitors and other anti-cancer agents. These treatments are effective against tumors that express molecular targets of immune checkpoint inhibitors. However, these therapies may be less effective against tumors that do not express the molecular targets of immune checkpoint inhibitors. These results show that novel therapies are needed for tumors that do not express molecular targets of immune checkpoint inhibitors.

PRIOR ART DOCUMENTS

Non-Patent Documents

Non-Patent Document 1: Zamarin, D., et al. Sci. Transl. Med. 2014; 6(226):226ra32.
Non-Patent Document 2: Fu, J., et al. Sci. Transl. Med. 2015; 7(283):283ra52.
Non-Patent Document 3: Kim, K., et al. Proc. Natl. Acad. Sci. U.S.A. 2014; 111(32)41774-9.
Non-Patent Document 4: John, L. B., et al. Clin. Cancer Res. 2013; 19(20)5636-46.
Non-Patent Document 5: Tumeh, P. C., et al. Nature. 2014; 515 (7528)568-71.

SUMMARY OF THE INVENTION

An object of the invention is to provide a therapeutic technique for treating immune checkpoint inhibitor-resistant tumors. Specifically, a very effective pretreatment anti-tumor drug (antigen-loaded nanogel and immunological enhancer) combined with T cell infusion therapy is provided.

The present inventors have studied effective therapies for immune checkpoint inhibitor-resistant tumors in which the expression of molecular targets of immune checkpoint inhibitors is low at the tumor site. As a pretreatment drug, a hydrophobized polysaccharide-based nanogel, in which a synthetic long chain peptide antigen or a recombinant protein antigen is loaded, and an immune-enhancing agent were used. It was found that a combination of administration of the pretreatment drug and subsequent infusion of antigen-specific T cells had a remarkable effect on tumors that are resistant to immune checkpoint inhibitors.

Representative, non-limiting embodiments of the present teachings are as follows.

1) A pharmaceutical composition for T cell infusion therapy against an immune checkpoint inhibitor-resistant tumor, which is a pharmaceutical composition to be administered prior to administration of antigen-specific T cells, comprising:

an antigen-loaded nanogel, in which one or more long chain peptide antigen(s) or one or more protein antigen(s) is (are) loaded in a hydrophobized polysaccharide-based nanogel, the one or more long chain peptide antigen(s) or one or more protein antigen(s) containing one or more CD8+ cytotoxic T cell recognition epitope(s) and/or one or more CD4+ helper T cell recognition epitope(s), which is/are derived from the antigen.

2) A pharmaceutical composition for T cell infusion therapy against an immune checkpoint inhibitor-resistant tumor, which is a pharmaceutical composition comprising T cells specific to said antigen to be administered after administration of said antigen-loaded nanogel, in which one or more long chain peptide antigen(s) or one or more protein antigen(s) is (are) loaded in a hydrophobized polysaccharide-based nanogel, the one or more long chain peptide antigen or one or more protein antigen containing one or more CD8+ cytotoxic T cell recognition epitope(s) and/or one or more CD4+ helper T cell recognition epitope(s), which is/are derived from the antigen.

In one embodiment of the present teachings, a recombinant protein antigen can be used as the long chain peptide antigen or the protein antigen. In such an embodiment, a nucleic acid having a nucleotide sequence encoding the recombinant protein that contains the predetermined amino acid sequence is prepared; after the recombinant protein is expressed by a cell (eukaryotic or prokaryotic) in which the nucleic acid has been incorporated, the recombinant protein antigen can be purified by known methods.

3) The pharmaceutical composition according to 1) or 2), further comprising an immune-enhancing agent which is administered with the antigen-loaded nanogel, or an immune-enhancing agent which is contained in the antigen-loaded nanogel.

4) The pharmaceutical composition according to any one of 1) to 3), wherein the antigen-specific T cell is a T cell that expresses a T cell receptor that recognizes the antigen or a chimeric antigen receptor that recognizes the antigen.

5) The pharmaceutical composition according to any one of 1) to 4), wherein the long chain peptide antigen is composed of 23 to 120 amino acid residues.

6) The pharmaceutical composition according to any one of 1) to 5), comprising a sequence selected from the group consisting of 2 to 10 tyrosines, 2 to 10 threonines, 2 to 10 histidines, 2 to 10 glutamines and 2 to 10 asparagines between the T cell recognition epitopes in the long chain peptide antigen.

7) The pharmaceutical composition according to any one of 1) to 6), wherein the hydrophobized polysaccharide comprises pullulan and cholesteryl groups.

8) The pharmaceutical composition according to any one of 3) to 7), wherein the immune-enhancing agent is at least one selected from the group consisting of TLR (Toll-like receptor) agonists (CpG oligo DNA or Poly-IC RNA), STING agonists or RLR (RIG-I-like receptors) agonists.

Of these, it is preferable to use a TLR agonist (CpG oligo DNA or Poly-IC RNA).

9) The pharmaceutical composition according to any one of 1) to 8), wherein the antigen is a tumor-specific antigen protein or a tumor stroma-specific antigen protein.

10) The pharmaceutical composition according to any one of 1) to 9), wherein the administration route of the antigen-loaded nanogel is at least one selected from the group consisting of subcutaneous, intradermal, intramuscular, intratumoral and intravenous.

11) The pharmaceutical composition according to any one of 1) to 10), wherein the antigen-loaded nanogel is administered at least 1 day prior to the administration of the pharmaceutical composition comprising the antigen-specific T cells.

12) A delivery system for selectively delivering a substance to tumor-associated macrophages when administered intravenously, comprising:

a nanogel having a particle size of 80 nm or less and composed of a hydrophobized polysaccharide containing pullulan and cholesteryl groups.

13) A non-human mammal tumor model for identifying effective therapeutic agents for immune checkpoint inhibitor-resistant tumors, wherein the tumor is murine fibrosarcoma CMS5a, and the non-human mammal is a mouse.

According to the present invention, useful pharmaceutical compositions can be provided for treating tumors that do not express molecular targets of immune checkpoint inhibitors and are resistant to immune checkpoint inhibitors. Enhancement of the anti-cancer activity of antigen-specific T cell infusions can be obtained by using an antigen-loaded nanogel that contains a hydrophobized polysaccharide-based nanogel as the delivery system, and a synthetic long chain peptide antigen or a recombinant protein antigen and an immune-enhancing agent as a pretreatment drug.

BRIEF DESCRIPTION OF THE FIGURES

FIG. 1(A) contains four photomicrographs showing the results of analyzing the expression of PD-L1 molecules in tumors locally after 7 days from being implanted, FIG. 1(B) is a graph showing the results of analyzing the PD-1 expression of CD3+ T cells localized in each tumor by flow cytometry, and FIG. 1(C) is a graph showing the results of the analysis of the number of CD8+ T cells that infiltrated into each tumor.

FIGS. 3(A)-3(C) depict three graphs showing the results of the therapeutic efficacy of antigen-specific T cell infusion on BALB/c mice that were subcutaneously transplanted with fibrosarcoma CMS5a tumors using a pretreatment drug that contains a long chain peptide antigen-loaded cholesteryl pullulan (CHP) nanogel and an immune-enhancing agent. FIG. 3(A) is a graph showing that antigen-specific T cell infusion after subcutaneous administration of the long chain peptide antigen-loaded CHP nanogel and CpG oligo DNA can heal CMS5a tumors, and that incomplete Freund's adjuvant (IFA), instead of the nanogel as the delivery system, can not heal CMS5a tumors, FIG. 3(B) is a graph showing that antigen-specific T cell infusion after intravenous administration of the long chain peptide antigen-loaded CHP nanogel and CpG oligo DNA can heal CMS5a tumors, and that intravenous administration of the antigen-loaded nanogel of the present invention has the same effect as subcutaneous administration, and FIG. 3(C) is a graph showing that antigen-specific T cell infusion after the administration of the long chain peptide antigen-loaded CHP nanogel and poly-IC RNA can heal CMS5a tumors, and that poly-IC RNA used as an immune-enhancing agent exhibits the same effect as CpG oligo DNA.

FIGS. 4(A)-4(C) depict three graphs showing the results of the therapeutic efficacy of antigen-specific T cell infusion on BALB/c mice that were subcutaneously transplanted with CMS5a tumors using a pretreatment drug that contains a long chain peptide antigen loaded CHP nanogel and an immune-enhancing agent. FIG. 4(A) is a graph showing that antigen-specific T cell infusion after the administration of the long chain peptide antigen loaded CHP nanogel and CpG oligo DNA can heal CMS5a tumors, and that CpG oligo DNA without the long chain peptide antigen-loaded CHP nanogel cannot heal CMS5a tumors, FIG. 4(B) is a graph showing that antigen-specific T cell infusion after the administration of the long chain peptide antigen-loaded CHP nanogel and CpG oligo DNA can heal CMS5a tumors, and that the long chain peptide antigen-loaded CHP nanogel without CpG oligo DNA can not heal CMS5a tumors, and FIG. 4(C) is a graph showing that antigen-specific T cell infusion after the administration of the long chain peptide antigen-loaded CHP nanogel and CpG oligo DNA can heal CMS5a tumors, and that the long chain peptide antigen-loaded CHP nanogel and CpG oligo DNA without the antigen-specific T cell infusion can not heal CMS5a tumors.

DETAILED DESCRIPTION

Embodiments of the Pretreatment Drug

Figure 1A:
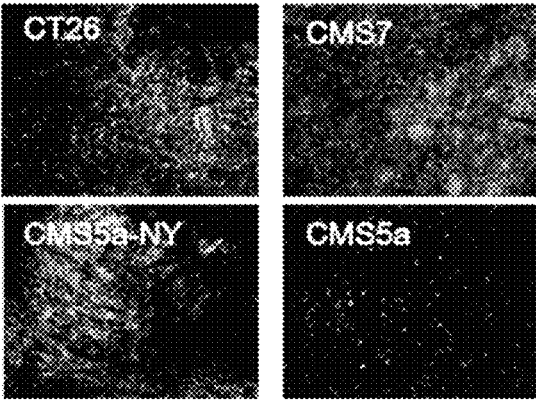
FIGS. 1(A)-1(C) show data indicating the expression of PD-L1 and PD-1, and the numbers of tumor-infiltrating CD8+ T cells for various mouse tumors implanted subcutaneously and engrafted into BALB/c mice.

Pretreatment drugs of the present teachings may comprise one or more immune-enhancing agents and a pharmaceutical composition, which contains a hydrophobized polysaccharide-based nanogel as a delivery system in which one or more synthetic long chain peptide antigens or recombinant protein antigens is (are) loaded, wherein the long chain peptide antigen(s) or the protein antigen(s) concurrently contains CD8+ cytotoxic T cell recognition epitope(s) and/or CD4+ helper T cell recognition epitope(s), which is (are) derived from a tumor-specific antigen protein or a tumor stroma-specific antigen.

The synthetic long chain peptide antigen preferably contains 23 to 120 amino acid residues and at least two T cell recognition epitopes. The synthetic long chain peptide antigen preferably contains 23 to 80 amino acids and at least two T cell recognition epitopes. The synthetic long chain peptide antigen preferably contains 23 to 60 amino acids and at least two T cell recognition epitopes.

The recombinant protein antigen preferably contains two or more T cell recognition epitopes and a tag sequence for purification if necessary, and is a full-length or partial-length antigen protein produced in *E. coli.*, insect cells or mammalian cells.

The CD8+ cytotoxic T cell recognition epitope(s) is (are) preferably (a) portion(s) of the amino acid sequence of a tumor-specific antigen protein or a tumor stroma-specific antigen protein. The CD4+ helper T cell recognition epitope(s) is (are) preferably (a) portion(s) of the amino acid sequence of a tumor-specific antigen protein or a tumor stroma-specific antigen protein.

The tumor-specific antigen protein is preferably selected from the group consisting of the MAGE family, NY-ESO-1/LAGE, SAGE, XAGE, HER2, PRAME, Ras, 5T4, WT1, p53, MUC-1, hTERT, RHAMM, Survivin, EGFRvIII, HPV E6, MART-1, gp100, CEA, IDO, Brachyury, Mesothelin, PSA and PSMA. The tumor stroma-specific antigen protein is preferably selected from the group consisting of FAP, the VEGFR family and TEM1.

The polysaccharide constituting the hydrophobized polysaccharide-based nanogel is preferably a pullulan or a mannan. The hydrophobic group(s) of the hydrophobized polysaccharide-based nanogel is (are) preferably cholesterol.

The hydrophobized polysaccharide-based nanogel is preferably non-ionic. The particle size of the hydrophobized polysaccharide-based nanogel is preferably 80 nm or less.

The immune-enhancing agent preferably includes a soluble TLR agonist, a soluble STING agonist or a soluble RLR agonist. As the soluble TLR agonist, CpG oligo DNA or poly-IC RNA are exemplified. As the soluble STING agonist, cyclic dinucleotides, such as CdGMP, and xanthenone-derivatives, such as DMXAA, are exemplified. As the soluble RLR agonist, 5'-phosphorylated double-stranded RNA is exemplified.

In the present invention, the synthetic long chain peptide antigen or the recombinant protein antigen is characterized in that it comprises at least two or more T cell recognition epitopes contained in a tumor-specific antigen protein and/or in a tumor stroma-specific antigen protein. T cell recognition epitopes are preferably those contained in a tumor-specific antigen protein or a tumor stroma-specific antigen protein. As such, they may be selected from MAGE family molecules such as MAGE-A1, MAGE-A2, MAGE-A3, MAGE-A4, MAGE-A5, MAGE-A6, MAGE-A8, MAGE-A9, MAGE-A10, MAGE-A11, MAGE-A12, MAGE-B1 and MAGE-B2, or T cell recognition epitopes contained in a tumor-specific antigen protein such as NY-ESO-1/LAGE molecule, SAGE, XAGE, HER2, PRAME, Ras, 5T4, WT1, p53, MUC-1, hTERT, RHAMM, Survivin, EGFRvIII, HPV E6, MART-1, gp100, CEA, IDO, Brachyury, Mesothelin, PSA and PSMA, or T cell recognition epitopes contained in tumor stroma-specific antigen proteins such as FAP, VEGFR family and TEM1. In T cell recognition epitopes, there are CTL epitopes recognized by CD8+ cytotoxic T cells and Th epitopes recognized by CD4+ helper T cells. The synthetic long chain peptide antigen or the recombinant protein antigen in the present invention preferably concurrently contains more than one each of the CTL epitopes and the Th epitopes. A long chain peptide antigen containing (a) CTL epitope(s) and a long chain peptide antigen containing (a) Th epitope(s) can be used alone or in combination.

The hydrophobized polysaccharide used in the present invention can be prepared by known methods. With regard to the polysaccharides in the hydrophobized polysaccharides, polymers in which sugar residues are glycosidically bound can be used without limitation. The sugar residues constituting the polysaccharide may be derived, for example, from monosaccharides, such as glucose, mannose, galactose, and fucose, or from disaccharides or oligosaccharides. The sugar residues may have 1,2-, 1,3-, 1,4- or 1,6-glycosidic bonds, and the bonds may be either α-type bonds or ß-type bonds. The polysaccharide may be linear or branched. Glucose residues may be preferably used as the sugar residues; pullulan, dextran, amylose, amylopectin, or mannan of natural or synthetic origin may be used as the polysaccharide; preferably mannan or pullulan can be used. The average molecular weight of the polysaccharide can range from 50,000 to 150,000.

As the hydrophobic group, for example, in a single-stranded and double-stranded chain, alkyl or sterol residues which are introduced at a rate of 1 to 5 per 100 monosaccharides (less than 5% by weight) are preferably used, at a rate of 1 to 3 per 100 monosaccharides (less than 3% by weight) are more preferably used. As the hydrophobic group, the alkyl groups or sterol residues are not limited; other residues can be used with good efficiency depending on the molecular weight or the isoelectric point of the encapsulated antigen. As the sterol residue, cholesterol, stigmasterol, beta-sitosterol, lanosterol and ergosterol residues are exemplified. Preferably, a cholesterol residue is used. As the alkyl group, ones having 20 or less carbon atoms are preferably used; ones having 10 to 18 carbon atoms are more preferably used. The alkyl group may be used in either a linear chain or a branched chain.

As the hydrophobized polysaccharide, one in which 1-5 primary hydroxyl groups per 100 sugars are linked to a polysaccharide of the following formula (I): $-O-(CH_2)_m$ $CONH(CH_2)_nNH-CO-O-R$ (I) (wherein R represents an alkyl group or a sterol residue; m represents 0 or 1; n represents any positive integer) is used preferably. As the alkyl group or the sterol residue, n is preferably 1 to 8.

As the hydrophobized polysaccharide, one that is linked via a linker can be used.

As the hydrophobized polysaccharide, a non-ionic one is preferably used. The zeta potential of the hydrophobized polysaccharide-based nanogel particles in which the synthetic long chain peptide antigen or the recombinant protein antigen is loaded is preferably from –2.0 mV to +2.0 mV under physiological conditions. The particle size of the hydrophobized polysaccharide-based nanogel in which the synthetic long chain peptide antigen or the recombinant protein antigen is loaded is preferably 80 nm or less.

The pretreatment drug of the present invention that comprises an immune-enhancing agent and a pharmaceutical composition, which contains a hydrophobized polysaccharide-based nanogel as the delivery system in which a synthetic long chain peptide antigen or a recombinant protein antigen is loaded, may be administered in various ways. Suitable non-oral administered routes, such as intravenous, intraperitoneal, subcutaneous, intradermal, adipose tissue, mammary gland tissue, inhalation or intramuscular, or mucosal route in the form of nasal drops, are preferably used.

The pretreatment drug of the present invention is typically prepared as a kit that contains the antigen-loaded nanogel mixed with an immune-enhancing agent or the antigen-loaded nanogel and an immune-enhancing agent separately. The agent may be prepared in a suitable dosage form for subcutaneous, intravenous, or intramuscular administration. The dose of the antigen-loaded nanogel necessary to induce the desired immunity can be appropriately determined. For example, the usual dose can be used in an amount of about 0.1 mg/administration to 10 mg/administration, as the synthetic long chain peptide antigen or the recombinant protein antigen. The number of times of administration is suitably 2 to 20 times. The administration interval between the pretreatment drug and the antigen-specific T cell infusion is selected between 1 day to 2 weeks.

Also disclosed herein is a therapeutic agent, which contains a cell population comprising antigen-specific T cells as the active ingredient, that may be used in combination with any of the pretreatment drugs according to the present teachings. The cell population suitable for the treatment of a patient is administered, for example, by intravenous injection or infusion, intraarterially, subcutaneously, or intraperitoneally. The cell population can be prepared as a drip infusion or injection according to methods known in the pharmaceutical field by mixing excipients, stabilizers, etc. with a known organic or inorganic carrier that is suited for non-oral administration. The content, the dose and other conditions of the cell population may be appropriately determined according to known immunotherapy. The content of the cell population in the pharmaceutical, without limitation, is preferably $1×10^3$ to $1×10^{11}$ cells/mL, more preferably $1×10^4$ to $1×10^{10}$ cells/mL, more preferably $1×10^5$ to $2×10^9$ cells/mL. The dosage of the therapeutic agent containing the cell population as the active ingredient, without limitation, is preferably $1 \times 10^6$ to $1 \times 10^{12}$ cells/day per adult, more preferably $1 \times 10^7$ to $5 \times 10^{11}$ cells/day per adult, more preferably $1 \times 10^8$ to $2 \times 10^{11}$ cells/day per adult. A step of introducing a foreign gene into the cell population can be included the manufacturing method of the cell population. "A foreign gene" means a gene that is artificially introduced into the cell population containing the target T cells, and also encompasses genes from the same species of the target cells. The means for introducing a foreign gene is not limited, and can be appropriately selected and used according to known gene introduction methods. Gene transfer can be carried out with a viral vector or without a viral vector. Many papers have been previously reported concerning these methods.

As the viral vector, without limitation, known viral vectors used for gene transfer, for example, such as retroviral vectors, lentiviral vectors, adenoviral vectors, adeno-associated virus vectors, simian viral vectors, vaccinia virus vectors, or Sendai viral vectors or the like, can be used. Retroviral vector or lentiviral vector, which can stably incorporate a foreign gene into a chromosomal DNA in targeted cells, preferably can be used. As the viral vector, those that lack replication ability preferably can be used so that they can not self-replicate in an infected cell. When a gene is transferred, a reagent for improving the gene transfer efficiency, such as RetroNectin® (Takara Bio), can be used. As for gene introduction methods without using viral vectors, methods using carriers such as liposomes or ligand-polylysine, calcium phosphate method, electroporation methods, or particle gun methods and the like can be used. In this case, a foreign gene integrated in plasmid DNA, in a linear DNA or in an RNA is introduced.

The foreign gene that is introduced is not particularly limited; any foreign genes can be used (for example, enzymes, cytokines, chemokines, or antigen receptors such as T-cell receptors (TCR) or chimeric antigen receptors (CAR), genes encoding proteins such as a receptor of a co-stimulant or ligand, antisense nucleic acids, siRNA, miRNA, ribozymes, and genes encoding aptamers). Foreign genes, for example, can be used by inserting into a vector or plasmid so as to be expressed under the control of a suitable promoter. Regulatory sequences such as enhancer sequences or terminator sequences can be incorporated within the vector.

A target of a therapeutic agent using an antigen-loaded nanogel, an immune-enhancing agents, and an antigen-specific T cell infusion is a human who has a tumor that is resistant to immune checkpoint inhibitors. Tumors types, such as prostate cancer, colon cancer, melanoma, head and neck cancer, esophageal cancer, stomach cancer, colorectal cancer, liver cancer, gallbladder-bile duct cancer, pancreatic cancer, lung cancer, breast cancer, ovarian cancer, bladder cancer, kidney cancer, testicular cancer, bone and soft tissue sarcoma, malignant lymphoma, leukemia, cervical cancer, skin cancer, brain tumors and the like, are exemplified without limitation.

Next, embodiments of the present invention will be explained in detail with reference to the figures. The technical scope of the invention is not limited by these examples and can be carried out in various forms without changing the gist of the invention.

Example 1

1. Materials and Methods

Anti-mouse CD16/CD32 antibody (clone 93), PE-labeled anti-mouse PD-L1 antibody (clone 9G2), APC-Cy7-labeled anti-CD45 antibody (clone 30-F11), and PE-Cy7-labeled anti-PD-1 antibody (clone 29F.1A12) were purchased from Biolegend. V450-labeled anti-CD8 antibody (clone 53-6.7) was purchased from eBioscience. Fetal bovine serum (FBS) was purchased from Bio-West. RPMI1640 medium (containing 2-mercaptoethanol) was purchased from the Cell Science Institute. Erythrocyte hemolysis solution (0.15 M $NH_4Cl$/10 mM $KHCO_3$/0.1 mM EDTA·$Na_2$ pH 7.2) was prepared at Mie University. Mouse colon cancer CT26 cell line (CRL-2638) was purchased from ATCC and was used as subcultured at Mie University. Mouse fibrosarcoma CMS7 cell line and murine fibrosarcoma CMS5a cell line were obtained from Memorial Sloan-Kettering Cancer Institute and were used as subcultured at Mie University. Human NY-ESO-1 antigen gene was obtained from Memorial Sloan-Kettering Cancer Institute. CMS5a-NY cell line, which is a CMS5a cell line stably transfected with human NY-ESO-1 antigen gene, was produced at Mie University, and was used as subcultured. Female BALB/c mice from 6-weeks-old to 12-weeks-old were purchased from Japan SLC and housed at the Mie University School of Medicine Animal Center. Protocols for animal experiments were approved by the ethics committee of the Mie University School of Medicine.

The mouse colon cancer CT26 cell line, BALB/c mice fibrosarcoma CMS7 cell line, mouse fibrosarcoma CMS5a cell line, and CMS5a-NY cell line were cultured in 10% FBS-containing RPMI1640 medium using T75 culture flasks (Corning). Each cell line was detached from the flasks using 0.5% trypsin-containing phosphate-buffered saline (PBS), and suspended in 10% FBS-containing RPMI1640 medium. The suspensions were centrifuged (400×g, 5 min, 4° C.) to remove the supernatants. The cells were washed twice with RPMI1640 medium and suspended in RPMI1640 medium at a concentration of $1 \times 10^6$/100 μL. The suspensions were subcutaneously implanted into the backs of the BALB/c mice at a dose of 100 μL/individual (3 mice per group).

Each cell line was implanted subcutaneously, and tumors were recovered after 1 week. Tumors were stained immunohistochemically in the following manner. Tumors embedded in O.C.T. compound (Sakura Finetech) were frozen and sliced into 3 μm thicknesses. The sliced tumor sections were air dried for 2 hours. Dried tumor sections were fixed with ice cold acetone for 15 minutes and used for immunostaining. After the tumor sections were washed 3 times with PBS, they were immersed in blocking solution (1% bovine serum albumin (BSA) and 5% Blocking One Histo (Nacalai Tesque) containing PBS) at 4° C. Anti-mouse CD16/CD32 antibody was diluted in blocking solution at a concentration of 1 μg/mL. The tumor sections were treated with the antibody solution for 30 minutes at room temperature in a humidified box to block Fcγ receptors. Next, the tumor sections were stained with PE-labeled anti-mouse PD-L1 antibody diluted at a concentration of 1 μg/mL in blocking solution for 1 hour at room temperature in a humidified box. After the tumor sections were washed three times with 0.02% Tween20-containing PBS, they were immersed in Prolong Gold antifade reagent with DAPI (Life Technologies). The tumor sections were observed with a fluorescent microscope BX53F (Olympus) or confocal laser scanning microscope LSM780 (Carl Zeiss). The microscopic images were processed using Photoshop Element (Adobe Systems).

Each cell line was implanted subcutaneously; after 1 week, immune cells that infiltrated the tumors were separated in the following manner. Tumors were isolated from the mice, crushed using gentleMACS (Miltenyi), and suspended in RPMI1640 medium. At this time, separated cells from 3 mice in a group were pooled. Collagenase D (final concentration 2 mg/mL, Roche) was added to the suspended cells, reacted for 30 minutes at 37° C., and the cells were crushed again using gentleMACS. The cells were filtered with a filter (22-µm pore size, BD Biosciences) and centrifuged (400×g, 5 min, 4° C.); the supernatant was removed and 2 mL of erythrocyte hemolysis solution was added to the cells. After one minute, 18 mL of RPMI1640 medium was added, and the cells were centrifuged (400×g, 5 min, 4° C.). After the supernatant was removed, the cells were suspended in RPMI1640 medium. After counting the number of cells, they were suspended in staining buffer (0.5% BSA-containing PBS) to yield a cell concentration of 3×10⁷ cells/mL. Per well, 50 µL of the cell suspensions were transferred to a 96-well V-bottom microplate (Nunc). The microplate was centrifuged (2000 rpm, 1 min, 4° C.). After removing the supernatant, the cells were suspended in 50 µL of staining buffer per well. APC-Cy7-labeled anti-mouse CD45 antibody, V450-labeled anti-mouse CD8 antibody, and PE-Cy7-labeled anti-mouse PD-1 antibody were added to the cells at the recommended usage concentrations of the manufacturer of each antibody. After mixing gently, they were allowed to stand in the dark for 15 minutes at 4° C. The cells were washed twice with 200 µL of staining buffer, suspended in 200 µL of staining buffer, and transferred to round-bottomed polystyrene tubes (BD Biosciences). The cells were analyzed using a flow cytometer FACS Canto II (BD Biosciences) and data analysis software FlowJo (Tree Star). The frequency of PD-1 expression was determined as expression frequencies (%) in the cell populations of CD45+ and CD8+. The frequency of CD8+ T cells was determined as the frequency (%) of CD8+ cells in the CD45+ cell population.

2. Results

Figure 1B:
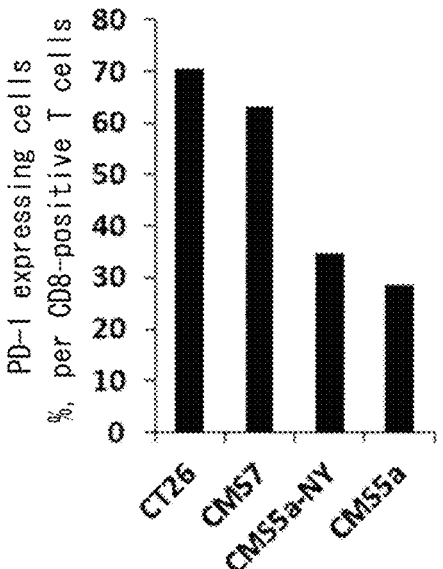
Figure 1C:
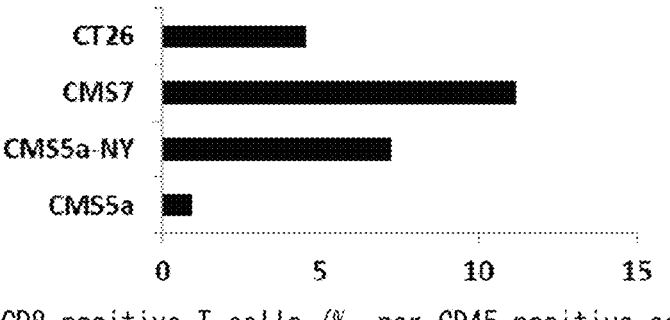

Immune checkpoint inhibitor-resistant human tumors exhibit the characteristics in that there is an expression-deficiency of immune checkpoint molecules and tumor-infiltration of CD8+ T cells is not observed (Non-patent Document 5). To search for a mouse tumor exhibiting the same characteristics, after various mouse cancer cell lines were implanted subcutaneously in BALB/c mice, tumors were harvested; expression of immune checkpoint molecules PD-L1 and PD-1 and the number of infiltrating CD4+ T cells were measured. FIG. 1(A) shows the results of the expression of PD-L1 molecules in CT26 tumors, CMS7 tumors, CMS5a-NY tumors and CMS5a tumors analyzed by immunostaining. Many cells expressing PD-L1 were observed in CT26 tumors, CMS7 tumors and CMS5a-NY tumors, whereas the number of PD-L1-expressing cells in CMS5a tumors was extremely small. FIG. 1(B) shows the results of the expression frequency of PD-1 in CD3+ T cells in tumor sites of tumors according to flow cytometry. Compared to the other tumors, the percentage of PD-1 expressing CD3+ T cells in CMS5a tumors was the lowest. FIG. 1(C) shows the frequency of CD8+ T cells that infiltrated into the tumor site of each tumor. Compared to other tumors, in CMS5a tumors the frequency of tumor-site-infiltrating CD8+ T cells was remarkably low. From these results, mouse tumor fibrosarcoma formed by implantation of the CMS5a cell line subcutaneously in mice was found to exhibit the same characteristics as immune checkpoint inhibitor-resistant human tumors.

12

Example 2

1. Materials and Methods

A hybridoma that expresses anti-mouse CTLA-4 antibody (clone 9D9) was obtained from Dr. James P. Allison at the MD Anderson Cancer Center, and antibody was prepared at Mie University. A hybridoma that expresses anti-mouse GITR antibody (clone DTA-1) was obtained from Dr. Shimon Sakaguchi at Osaka University, and antibody was prepared at Mie University. Anti-mouse-PD-1 antibody (clone RMP1-14) was obtained from Dr. Hideo Yagita at Juntendo University. Fetal bovine serum (FBS) was purchased from Bio-West. RPMI1640 medium (containing 2-mercaptoethanol) was purchased from the Cell Science Institute. Mouse colon cancer CT26 cell line (CRL-2638) was purchased from ATCC and was used as subcultured at Mie University. Mouse fibrosarcoma CMS7 cell line and murine fibrosarcoma CMS5a cell line were obtained from Memorial Sloan-Kettering Cancer Institute and were used as subcultured at Mie University. Human NY-ESO-1 antigen gene was obtained from Memorial Sloan-Kettering Cancer Institute. CMS5a-NY cell line, which is a CMS5a cell line stably transfected with human NY-ESO-1 antigen, was produced at Mie University, and was used as subcultured. Female BALB/c mice from 6-weeks-old to 12-weeks-old were purchased from Japan SLC and housed at the Mie University School of Medicine Animal Center. Protocols for animal experiments were approved by the ethics committee of the Mie University School of Medicine.

The CT26 cell line, CMS7 cell line, CMS5a cell line, and CMS5a-NY cell line were cultured in 10% FBS-containing RPMI1640 medium using T75 culture flasks (Corning). Each cell line was detached from the flasks using 0.5% trypsin-containing phosphate buffer saline (PBS), and suspended in 10% FBS-containing RPMI1640 medium. The suspensions were centrifuged (400×g, 5 min, 4° C.) to remove the supernatants. The cells were washed twice with RPMI1640 medium and suspended in RPMI1640 medium at a concentration of 1×10⁶/100 µL. The suspensions were subcutaneously implanted in the backs of the BALB/c mice at a dose of 100 µL/individual (4 mice per group). Anti-mouse PD-1 antibody diluted in PBS (150 µg), anti-mouse CTLA-4 antibody diluted in PBS (100 µg) and anti-mouse GITR antibody diluted in PBS (100 µg) were intraperitoneally administered as immune checkpoint inhibitors simultaneously at 7, 9 and 11 days after the tumor implantation. The length and breadth of the tumors were measured after the tumor transplantation over time, and the tumor volumes were calculated according to the formula: (longer diameter× shorter diameter×shorter diameter×0.5). Statistical analysis was performed by non-parametric test using Microsoft Excel (Microsoft).

2. Results

Figure 2:
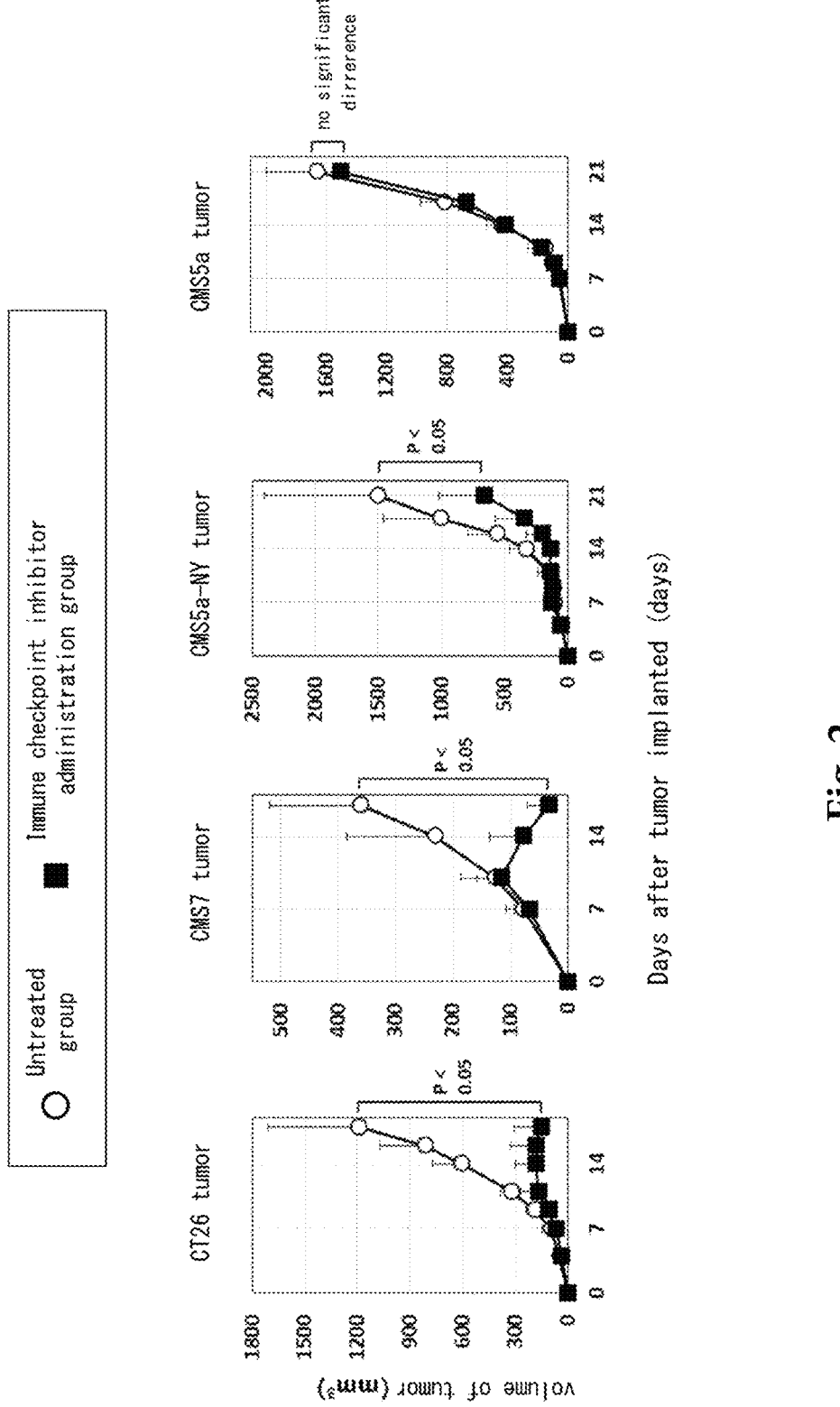
FIG. 2 depicts four graphs showing the results of examining the susceptibility to immune checkpoint inhibitors of various mouse tumors implanted subcutaneously and engrafted into BALB/c mice.

From the results in Example 1, tumors formed by subcutaneously implanted murine fibrosarcoma CMS5a cell line in BALB/c mice were expected to be resistant to immune checkpoint inhibitors. Therefore, combination therapy was attempted using anti-PD-1 antibody, anti-CTLA-4 antibody and anti-GITR antibody as immune checkpoint inhibitors to BALB/c mice with tumors formed by subcutaneously implanted mouse cancer cell lines. The results were shown in FIG. 2. The inhibition effects on tumor growth by the combination therapy using the immune checkpoint inhibitors were observed clearly in CT26 tumors, CMS7 tumors and CMS5a-NY tumors. In contrast, the combination therapy using the immune checkpoint inhibitors did not have any effect on CMS5a tumors; they showed similar growth as the untreated group. Therefore, the CMS5a tumors were proved to exhibit strong resistance to immune checkpoint inhibitors. Together with the results of Example 1, CMS5a tumors were considered to be a good model of immune checkpoint inhibitor-resistant human tumors. It became clear that effective treatments for immune checkpoint inhibitor-resistant human tumors were to be examined by using CMS5a tumors as the evaluation system.

Example 3

1. Materials and Methods

Cholesteryl pullulan (abbreviation CHP, trade name CHP-80T) was obtained from NOF Corporation. Incomplete Freund's adjuvant (abbreviation IFA, product number F5506) was purchased from Sigma-Aldrich. Long chain peptide antigen-loaded CHP nanogel was prepared as follows. Long peptides antigens (MEN peptide: SNPARYE-FLYYYYYYQYIHSANVLYYYYYYRGPESRLL (SEQ ID NO: 1) and p121 peptide: NDHIAYFLYQILRGLQYIH-SANVLHRDLKPSNLLLNT (SEQ ID NO: 2)) were chemically synthesized by Bio-Synthesis and were dissolved in dimethyl sulfoxide (abbreviation DMSO, Nacalai Tesque) at a concentration of 10 mg/mL. CHP was dissolved in phosphate-buffered saline (PBS) containing 6 M urea (Nacalai Tesque) at a concentration of 10 mg/mL. One mL (10 mg) of the long chain peptide antigen solution and 20 mL (200 mg) of the CHP solution were mixed and left overnight with gentle stirring at 4° C. in the dark. The mixture was transferred to a dialysis membrane (molecular weight: 3,500, Thermo Scientific), and dialyzed against PBS containing 0.6 M urea as the external dialysis solution in a volume ratio of 100 times or more for 2 hours to overnight at 4° C. Furthermore, dialysis was performed using PBS containing 0.06 M urea as the external dialysis solution in a volume ratio of 100 times for 2 hours to overnight at 4° C. Again, dialysis was performed using PBS as the external dialysis solution in a volume ratio of 100 times or more for 2 hours to overnight at 4° C. The dialysis internal solution was recovered and filtered using a sterilized filter with a 0.22 μm pore size (PVDF membrane, Millipore). After filtration, the UV absorbance at 280 nm was measured using Nanodrop 2000 (Thermo Scientific). The final concentration of the long chain peptide antigen was determined with a molecular extinction coefficient (1 mg/mL=4.181).

The long chain peptide antigen:IFA mixture was prepared as follows. The long chain peptide antigen was dissolved at a concentration of 60 μg/125 μL in PBS containing 25% DMSO and collected into a syringe. Separately, 125 μL of IFA was drawn into another syringe. After both syringes were connected by a three-way stopcock, suctioning and discharging by the syringes were repeated. After mixing well, the solution was used for administration. Fetal bovine serum (FBS) was purchased from Bio-West. RPMI1640 medium (containing 2-mercaptoethanol) was purchased from the Cell Science Institute. Mouse fibrosarcoma CMS5a cell line was obtained from Memorial Sloan-Kettering Cancer Institute, and was used as subcultured at Mie University. Mouse fibrosarcoma CMS5a cell line expresses mutated ERK2 protein. A peptide containing the mutation site of the mutated ERK2 protein (QYIHSANVL: SEQ ID NO: 3, the underline indicates the mutation) is recognized by CD8+ cytotoxic T cells of BALB/c mice. A T cell receptor (TCR)

that recognizes the mutant peptide was isolated, and TCR gene-introduced mice (DUC18 mice) have been produced. The long chain peptide antigens used in the example (MEN peptide and p121 peptide) contain a CD8+ cytotoxic T-cell recognition epitope sequence of the mutated ERK2 (QYIH-SANVL: SEQ ID NO. 3).

Female BALB/c mice from 6-weeks-old to 12-weeks-old were purchased from Japan SLC. DUC18 mice were obtained from the University of Washington, and were used as bred at Mie University. The mice were bred at the Mie University School of Medicine Animal Center. Protocols for animal experiments were approved by the ethics committee of the Mie University School of Medicine.

Mouse fibrosarcoma CMS5a cell line was cultured in 10% FBS-containing RPMI1640 medium using a T75 culture flask (Corning). The cell line was detached from the flask using 0.5% trypsin-containing PBS and suspended in 10% FBS-containing RPMI1640 medium. The suspension was centrifuged (400×g, 5 min, 4° C.) to remove the supernatant. The cells were washed twice with RPMI1640 medium and suspended in RPMI1640 medium at a concentration of $1 \times 10^6 / 100$ μL. The suspension was subcutaneously implanted in both sides of the backs of BALB/c mouse at a dose of 100 μL/individual (4 mice per group). In case the antigen loaded nanogel and an immune enhancer were to be administered as the pretreatment drug, at 7 days and 11 days after tumor implantation, the long chain peptide antigen-loaded CHP nanogel or the long chain peptide antigen:IFA mixture was administered subcutaneously into the backs or tail veins of the mice together with 50 μg of CpG oligo DNA1668 (Gene Design) or 50 μg of Poly-ICLC RNA (Oncovir) in PBS as the immune-enhancing agent. In the experiment shown in FIG. 4(A), the p121 peptide was used as the long chain peptide antigen. In the other experiments, the MEN peptide was used. CD8+ T cells in the spleen of mutated ERK2-specific TCR transgenic mice (DUC18 mice) were isolated using a CD8a+ T Cell Isolation Kit (Miltenyi). Isolated CD8+ T cells were suspended in RPMI1640 medium at a concentration of $2 \times 10^6$ cells/200 μL. After 8 days and 12 days from tumor implantation, isolated CD8+ T cells were infused from within the tail vein as antigen-specific T cells for the treatment. Statistical analysis was performed by non-parametric test using Microsoft Excel (Microsoft).

2. Results

An effective treatment for immune checkpoint inhibitor-resistant human tumors was investigated using CMS5a tumors, which formed by being implanted subcutaneously in BALB/c mice, as the evaluation system. As a result, as shown in FIG. 3(A), the proliferation of CMS5a tumors was significantly inhibited by antigen-specific T cell infusion after subcutaneous administration of the long chain peptide antigen-loaded CHP nanogel and the immune-enhancing agent (CpG oligo DNA) as the pretreatment drug. A therapeutic effect was not observed in the case of using IFA as the delivery system. As shown in FIG. 3(B), intravenous administration of the pretreatment drug, instead of subcutaneous administration, also was found to be effective. As shown in FIG. 3(C), poly-IC RNA as the immune-enhancing agent in the pretreatment drug, instead of CpG oligo DNA, also was found to be effective.

As shown in FIG. 4(A), a pretreatment drug that omitted the long chain peptide antigen loaded CHP nanogel was found to be not effective. As shown in FIG. 4(B), a pretreatment drug that omitted the immune-enhancing agent (CpG oligo DNA) was found to be not effective. These results showed that the pretreatment drug of the antigen-specific T cell infusion must contain a long chain peptide antigen-loaded CHP nanogel and an immune-enhancing agent. As shown in FIG. 4(C), when the antigen-specific T cell infusion was omitted, administration of only the pretreatment drug was found to be not effective.

Thus, the pretreatment drug of the invention, when combined with the antigen-specific T cell infusion, was found to treat immune checkpoint inhibitor-resistant tumors.

Example 4

1. Materials and Methods

Rhodamine-labeled CHP nanogel was obtained from Dr. Kazunari Akiyoshi at Kyoto University. APC-Cy7-labeled anti-mouse CD45 antibody (clone 30-F11), FITC-labeled anti-mouse CD8 antibody (clone 53-6.7), PE-labeled anti-mouse CD11b antibody (clone M1/70), Pacific blue-labeled anti-mouse F4/80 antibody (clone BM8) and PE-Cy7-labeled anti-mouse CD11c antibody (clone N418) were purchased from BioLegend. PerCP-Cy5.5-labeled anti-mouse CD4 antibody (clone RM4-5) was purchased from BD Biosciences. APC-labeled anti-mouse B220 antibody (clone RA3-6B2) was purchased from eBioscience. Fetal bovine serum (FBS) was purchased from Bio-West. RPMI1640 medium (containing 2-mercaptoethanol) was purchased from the Cell Science Institute. Erythrocyte hemolysis solution ($0.15$ M $NH_4Cl/10$ mM $KHCO_3/0.1$ mM $EDTA \cdot Na_2$ pH 7.2) was prepared at Mie University. Mouse fibrosarcoma CMS5a cell line was obtained from Memorial Sloan-Kettering Cancer Institute and was used as subcultured at Mie University. Female BALB/c mice from 6-weeks-old to 12-weeks-old were purchased from Japan SLC and housed at the Mie University School of Medicine Animal Center. Protocols for animal experiments were approved by the ethics committee of the Mie University School of Medicine.

The mouse fibrosarcoma CMS5a cell line was cultured in 10% FBS-containing RPMI1640 medium using a T75 culture flask (Corning). The cell line was detached from the flask using 0.5% trypsin-containing phosphate buffer saline (PBS), and suspended in 10% FBS-containing RPMI1640 medium. The suspension was centrifuged ($400 \times g$, 5 min, 4° C.) to remove the supernatant. The cells were washed twice with RPMI1640 medium. The cells were suspended in RPMI1640 medium at a concentration of $1 \times 10^6/100$ µL; the cells were implanted subcutaneously into the backs of BALB/c mice at a dose of 100 µL/individual (4 per group). After 7 days from tumor implantation, 1 mg of Rhodamine-labeled CHP nanogel (10 mg/mL PBS) was subcutaneously administered to the backs or to the tail vein. On the next day after the Rhodamine-labeled CHP nanogel administration, tumor-infiltrating immune cells were separated by the following method. Tumors were isolated from the mice, crushed using gentleMACS (Miltenyi) and suspended in RPMI1640 medium. Separated cells from 4 mice in a group were pooled. Collagenase D (final concentration 2 mg/ml, Roche) was added to suspended cells, reacted for 30 min at 37° C., and the cells were crushed again using gentleMACS. The cells were filtered with a filter (22-µm pore size, BD Biosciences) and centrifuged ($400 \times g$, 5 min, 4° C.); the supernatant was removed and 2 mL of erythrocyte hemolysis solution was added to the cells. After one minute, 18 mL of RPMI1640 medium was added, and the cells were centrifuged ($400 \times g$, 5 min, 4° C.). After the supernatant was removed, the cells were suspended in RPMI1640 medium.

After counting the number of cells, they were suspended in staining buffer (0.5% bovine serum albumin-containing PBS) to yield a cell concentration of $3 \times 10^7$ cells/mL. Fifty micro liters of the cell suspension per well were transferred into a 96-well V-bottom microplate (Nunc). The microplate was centrifuged (2000 rpm, 1 min, 4° C.); after removing the supernatant, the cells were suspended in 50 µL of staining buffer per well. After 18 hours from the Rhodamine-labeled CHP nanogel administration, regional lymph nodes were collected. In the case of subcutaneous administration, lymph nodes of the administration site (the inguinal lymph nodes) were collected; in the case of intravenous administration, tumor draining lymph nodes (inguinal lymph nodes) were collected.

After grinding the lymph nodes using a glass slide, released cells were suspended in RPMI1640 medium. At this time, cells from 4 mice in a group were pooled. The suspension was centrifuged ($400 \times g$, 5 min, 4° C.) to remove the supernatant, and the cells were treated for 1 min by adding 2 mL of erythrocyte hemolysis solution. 18 mL of RPMI1640 medium was added, and the cells were centrifuged ($400 \times g$, 5 min, 4° C.).

After removing the supernatant, the cells were suspended in RPMI1640 medium. The cell suspension was centrifuged ($400 \times g$, 5 min, 4° C.) and the supernatant was removed. The cells were washed twice with 2% FBS-containing PBS, and suspended. APC-Cy7-labeled anti-mouse CD45 antibody, FITC-labeled anti-mouse CD8 antibody, PerCP-Cy5.5-labeled anti-mouse CD4 antibody, APC-labeled anti-mouse B220 antibody, PE-labeled anti-mouse CD11b antibody, Pacific blue-labeled anti-mouse F4/80 antibody, and PE-Cy7-labeled anti-mouse CD11c antibody were added at the recommended usage concentrations of the manufacturer of each antibody to cell suspensions prepared from the tumors or lymph nodes. After mixing, they were allowed to stand in the dark for 15 minutes at 4° C. The cells were washed twice with 200 µL of staining buffer, re-suspended in 200 µL of staining buffer, and transferred to round-bottomed polystyrene tubes (BD Biosciences). The cells were analyzed using a flow cytometer FACS Canto II (BD Biosciences) and data analysis software FlowJo (Tree Star).

T cells were detected as CD45+ and CD4+, or CD45+ and CD8+; B cells were detected as CD45+ and B220+, macrophages were detected as CD45+ and CD11b+ and CD11c+ and F4/80+. The Rhodamine+ cells in each of the immune cells were detected as CHP nanogel uptake cells.

2. Results

Figure 5:
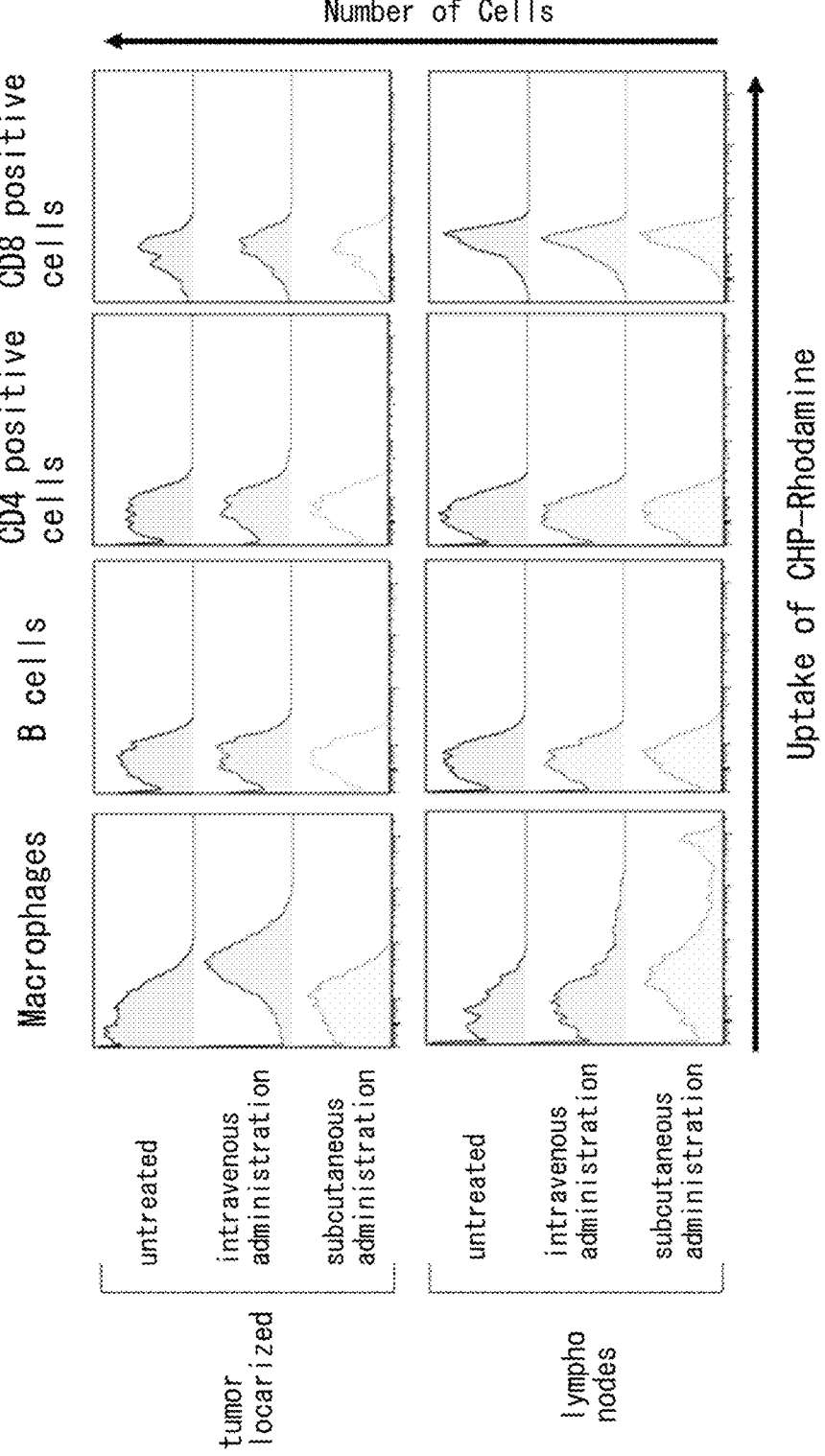
FIG. 5 depicts data showing the results of an uptake assay of CHP nanogels into tumor-associated immune cells when the CHP nanogel was administered intravenously to BALB/c mice in which CMS5a tumors were implanted subcutaneously.

As shown in FIG. 3(B), the pretreatment drug of the invention showed similar therapeutic effects against the immune checkpoint inhibitor-resistant CMS5a tumors in both subcutaneous and intravenous administration. To elucidate the mechanism of action of the pretreatment drug, after subcutaneous or intravenous administration of the Rhodamine-labeled CHP nanogel into BALB/c mice, into which the CMS5a tumors had been implanted subcutaneously, the uptake of CHP nanogel into immune cells was measured in lymph nodes and tumor sites. As shown in FIG. 5, subcutaneously administered CHP nanogel was taken up well into macrophages of administered regional lymph nodes. On the other hand, intravenously administered CHP nanogel was taken up well into tumor-associated macrophages. Uptake into other immune cells was not observed. It was thought that the activity of antigen-specific T cells is enhanced by lymph nodes or tumor-associated macrophages taking up the long chain peptide antigens delivered by CHP nanogel and presenting to infused antigen-specific T cells. When the CHP nanogel is administered intravenously, it may be selectively delivered to tumor-associated macrophages.

Example 5

1. Materials and Methods

Fetal bovine serum (FBS) was purchased from Bio-West. RPMI1640 medium (containing 2-mercaptoethanol) was purchased from the Cell Science Institute. Erythrocyte hemolysis solution (0.15 M $NH_4Cl$/10 mM $KHCO_3$/0.1 mM $EDTA \cdot Na_2$ pH 7.2) was prepared at Mie University. Mouse fibrosarcoma CMS5a cell line was obtained from Memorial Sloan-Kettering Cancer Institute, and was used as subcultured at Mie University. Female BALB/c mice from 6-weeks-old to 12-weeks-old were purchased from Japan SLC. Mutated ERK2-specific TCR transgenic mice (DUC18 mice) were obtained from the University of Washington, and were used as bred at Mie University. The mice were bred at the Mie University School of Medicine Animal Center. Protocols for animal experiments were approved by the ethics committee of the Mie University School of Medicine.

The mouse fibrosarcoma CMS5a cell line was cultured in 10% FBS-containing RPMI1640 medium using a T75 culture flask (Corning). The cell line was detached from the flask using 0.5% trypsin-containing PBS, and suspended in 10% FBS-containing RPMI1640 medium. The suspension was centrifuged (400×g, 5 min, 4° C.) to remove the supernatant. The cells were washed twice with RPMI1640 medium and suspended in RPMI1640 medium at a concentration of $1 \times 10^6$/100 μL. The suspension was subcutaneously implanted in both sides of the backs of BALB/c mouse at a dose of 100 μL/individual (5 mice per group). At 7 days after tumor implantation, a long chain peptide antigen-loaded CHP nanogel (60 μg as MEN peptide, dissolved in PBS), which was prepared in the same manner as in Example 3, and CpG oligo DNA1668 (50 μg, dissolved into PBS, Gene Design) were admixed and administered into the tail vein. 18 hours later, antigen presenting cells from tumor, lung, liver, spleen and lymph nodes of treated mice were separated by the method shown below.

The isolation kit made by Miltenyi (Tumor Dissociation Kit (Part No. 130-096-730)) for tumors, the isolation kit made by Miltenyi (Lung Dissociation Kit (Part No. 130-095-927)) for lung, and the isolation kit made by Miltenyi (Liver Dissociation kit (Part No. 130-105-807))) for liver, were respectively used. After treatment according to the manufacturer's recommended protocol, isolated cells were suspended in RPMI1640 medium.

At this time, cells from 5 mice in a group were pooled. The suspensions were centrifuged (400×g, 5 min, 4° C.) to remove supernatant, and the cells were treated for 1 min by adding 2 mL of erythrocyte hemolysis solution. 18 mL of RPMI1640 medium was added, and the cells were centrifuged (400×g, 5 min, 4° C.). After removing the supernatant, the cells were suspended in RPMI1640 medium. After the spleen and inguinal lymph nodes were triturated with a glass slide, released cells were collected in RPMI1640 medium. At this time, cells from 5 mice in a group were pooled. The suspensions were centrifuged (400×g, 5 min, 4° C.) to remove the supernatant, and the cells were treated for 1 minute by adding 2 mL of erythrocyte hemolysis solution. 18 mL of RPMI1640 medium was added, and the cells were centrifuged (400×g, 5 min, 4° C.). After removing the supernatant, the cells were suspended in RPMI1640 medium (it was called "the primary cell suspension"). The primary cell suspension prepared from each tissue was centrifuged (400×g, 5 min, 4° C.) and the supernatant was removed. After the cells were washed twice with 2% FBS-containing PBS, they were suspended in 2% FBS-containing PBS. The suspension was called "the secondary cell suspension". CD11b+ cells were isolated from the secondary cell suspension using CD11b microbeads (Miltenyi). These cells were used as antigen presenting cells from each tissue. On the other hand, CD8+ T cells were isolated from the spleen of DUC18 mice in the same manner as in Example 3. Then, responder T cells were prepared by labeling with the fluorescent dye CFSE (Thermo Fisher Science). $2.5 \times 10^5$ cells of antigen presenting cells and $2 \times 10^5$ cells of responder T cells per well were added to a 96-well V-bottom microplate (Nunc), and co-cultured for 72 hours in 10% FBS-containing RPMI1640 medium. When the responder T cells proliferate in response to antigen presentation, the fluorescence of CFSE is attenuated with the cell division. The change of the fluorescence was measured using a flow cytometer FACS Canto II (BD Biosciences) and data analysis software FlowJo (Tree Star). The percentage of responder T cells that divided more than once was calculated, and the antigen presenting ability of antigen-presenting cells from each tissue was evaluated.

2. Results

In Example 4, it was revealed that intravenously administered CHP nanogel was taken up selectively by tumor-associated macrophages. It was considered that the long chain peptide antigen-loaded CHP nanogels administered intravenously were taken up into tumor-associated macrophages, and the antigen was presented to the infused antigen-specific T cells to enhance the activity of the antigen-specific T cells. The following experiments were performed to confirm the antigen-presenting activity of tumor-associated macrophages. CD11b+ macrophages in tumors or various tissues were isolated from BALB/c mice in which CMS5a tumors had been implanted subcutaneously; CHP nanogel, which was loaded with a long chain peptide antigen containing the CD8+ T cell recognition epitope of mutated ERK2, and CpG oligoDNA were intravenously administered. The CD11b+macrophages as antigen-presenting cells were co-cultured in vitro with the CD8+ T cells from mutated ERK2-specific TCR transgenic mice. If the CD11b+ macrophages present the CD8+ T cell recognition epitope of the mutated ERK2 derived from the administered long chain peptide antigen, the CD8+ T cells from mutated ERK2-specific TCR transgenic mice are activated and proliferate. The fluorescence was measured by CFSE dilution test using flow cytometry to estimate the T cell proliferation and was used as an indicator of antigen presentation.

Figure 6:
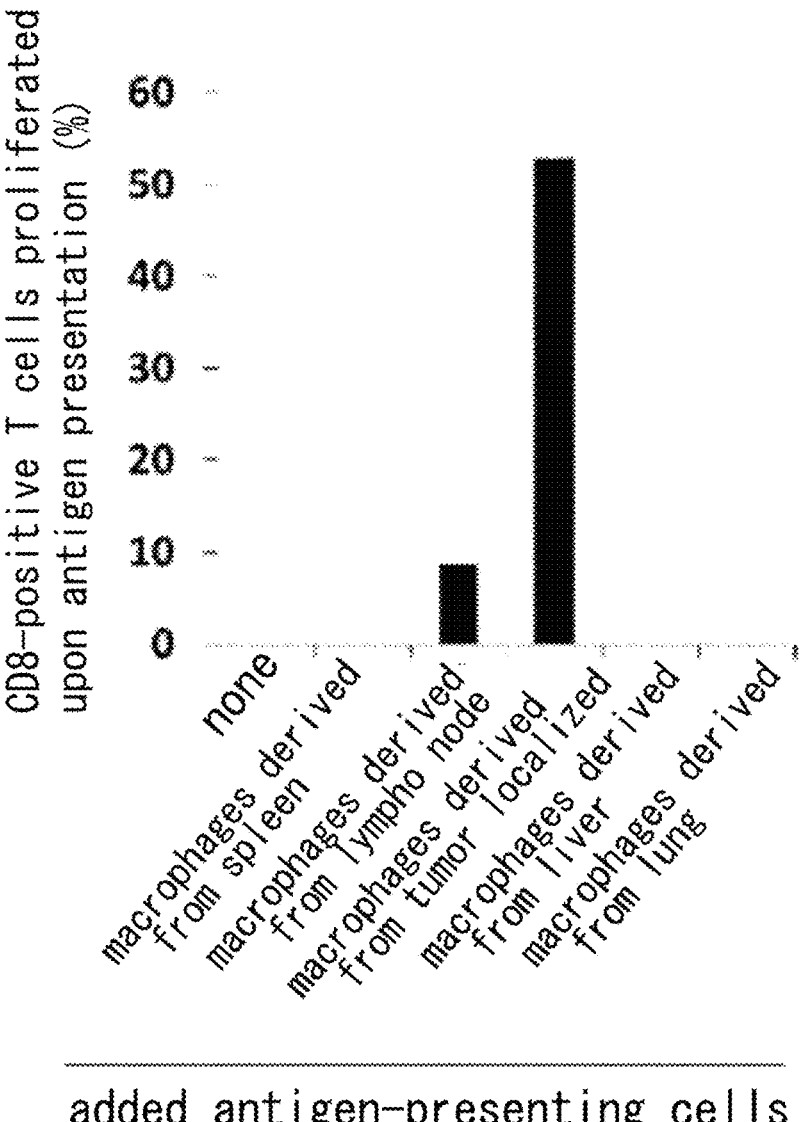
FIG. 6 depicts data showing the results of analysis of antigen presenting activity of tumor-associated macrophages when the long chain antigen-loaded CHP nanogels and CpG oligo DNA were administered to BALB/c mice in which CMS5a tumors were implanted subcutaneously.

As shown in FIG. 6, when a long chain peptide antigen-loaded CHP nanogel and CpG oligoDNA were administered intravenously, the long chain peptide antigen was presented by tumor-associated macrophages. Macrophages from lymph nodes were observed to present the long chain peptide antigen weakly. Macrophages from other tissues were not observed to present the long peptides antigen. It was thought that these macrophages did not take up the long chain peptide antigen-loaded CHP nanogel and CpG oligoDNA, or may lack the ability to present the antigen. These results showed that, when the CHP nanogel is administered intravenously, the CHP nanogel has the ability to selectively transport molecules, in particular antigen, to tumor-associated macrophages and to cause the antigen to be presented.

The mechanism has been thought to be the same in non-human mammals, including monkey, mouse, rat, pig, cattle, and dog. The composition of the invention is believed to have the same effect on humans, monkeys, mice, rats, pigs, cattle, dogs, etc.

According to these embodiments, it was possible to provide a therapeutic technique for treating immune checkpoint inhibitor-resistant tumors that do not express molecular targets of immune checkpoint inhibitors. The enhancement of the anti-cancer activity of antigen-specific T cell infusion was derived by a synthetic long chain peptide antigen or recombinant protein antigen loaded-nanogel using a hydrophobized polysaccharide-based nanogel as the delivery system and an immunological enhancer, serving as a pretreatment drug.

least one selected from the group consisting of TLR (Toll-like receptor) agonists, STING agonists or RLR (RIG-I-like receptors) agonists.

3. The method according to claim 2, wherein the immune-enhancing agent is contained in the antigen-loaded nanogel.

4. The method according to claim 1, wherein the antigen-specific T cell is a T cell that expresses a T cell receptor that recognizes the antigen or a chimeric antigen receptor that recognizes the antigen.

5. The method according to claim 1, wherein the long peptide antigen or protein antigen comprises a sequence selected from the group consisting of 2 to 10 tyrosines, 2 to 10 threonines, 2 to 10 histidines, 2 to 10 glutamines and 2 to 10 asparagines between the T cell recognition epitopes in the long chain peptide antigen.

SEQUENCE LISTING

```
Sequence total quantity: 3
SEQ ID NO: 1              moltype = AA   length = 38
FEATURE                  Location/Qualifiers
REGION                   1..38
                         note = MEN peptide
source                   1..38
                         mol_type = protein
                         organism = synthetic construct
SEQUENCE: 1
SNPARYEFLY YYYYYQYIHS ANVLYYYYYY RGPESRLL                        38

SEQ ID NO: 2              moltype = AA   length = 37
FEATURE                  Location/Qualifiers
REGION                   1..37
                         note = p121 peptide
source                   1..37
                         mol_type = protein
                         organism = synthetic construct
SEQUENCE: 2
NDHIAYFLYQ ILRGLQYIHS ANVLHRDLKP SNLLLNT                         37

SEQ ID NO: 3              moltype = AA   length = 9
FEATURE                  Location/Qualifiers
REGION                   1..9
                         note = CD8+ epitope
source                   1..9
                         mol_type = protein
                         organism = synthetic construct
SEQUENCE: 3
QYIHSANVL                                                        9
```

The invention claimed is:

1. A method for treating an immune checkpoint inhibitor-resistant tumor in a patient in need thereof, comprising:

administering to the patient a therapeutically effective amount of an antigen-loaded nanogel comprising a long peptide antigen or a protein antigen composed of 23 to 120 amino acid residues loaded in a hydrophobized polysaccharide, the long peptide antigen or protein antigen containing a CD8+ cytotoxic T cell recognition epitope and/or a CD4+ helper T cell recognition epitope, which is/are derived from a tumor-specific antigen protein or a tumor stroma-specific antigen protein; and at least 1 day thereafter, administering to the patient a therapeutically effective amount of antigen-specific T cells that bind to an antigen of the immune checkpoint inhibitor-resistant tumor.

2. The method according to claim 1, further comprising administering an immune-enhancing agent with the antigen-loaded nanogel, wherein the immune-enhancing agent is at 6. The method according to claim 1, wherein the hydrophobized polysaccharide comprises pullulan and cholesteryl groups.

7. The method according to claim 1, wherein the CD8+ cytotoxic T cell recognition epitope and/or the CD4+ helper T cell recognition epitope is/are derived from a tumor-specific antigen protein.

8. The method according to claim 1, wherein the antigen-loaded nanogel is administered according to an administration route selected from the group consisting of subcutaneous, intradermal, intramuscular, intratumoral and intravenous.

9. The method according to claim 1, wherein the antigen-loaded nanogel has a particle size of 80 nm or less and the hydrophobized polysaccharide contains pullulan and cholesteryl groups.

10. The method according to claim 9, wherein the antigen-loaded nanogel is administered according to an administration route selected from the group consisting of subcutaneous, intradermal, intramuscular, intratumoral and intravenous.

11. The method according to claim 10, wherein the antigen-specific T cell is a T cell that expresses a T cell receptor that recognizes the antigen or a chimeric antigen receptor that recognizes the antigen.

12. The method according to claim 11, further comprising administering an immune-enhancing agent with the antigen-loaded nanogel, wherein the immune-enhancing agent is at least one selected from the group consisting of TLR (Toll-like receptor) agonists, STING agonists or RLR (RIG-I-like receptors) agonists.

13. The method according to claim 12, wherein the long peptide antigen or protein antigen comprises a sequence selected from the group consisting of 2 to 10 tyrosines, 2 to 10 threonines, 2 to 10 histidines, 2 to 10 glutamines and 2 to 10 asparagines between the T cell recognition epitopes in the long chain peptide antigen.

14. The method according to claim 13, wherein the immune-enhancing agent is at least one selected from the group consisting of TLR (Toll-like receptor) agonists, STING agonists or RLR (RIG-I-like receptors) agonists.

15. The method according to claim 14, wherein the CD8+ cytotoxic T cell recognition epitope and/or the CD4+ helper T cell recognition epitope is/are derived from a tumor-specific antigen protein.

16. The method according to claim 15, wherein the long peptide antigen or protein antigen is derived from human NY-ESO-1.

17. The method according to claim 1, wherein the therapeutically effective amount of the antigen-specific T cells that bind to an antigen of the immune checkpoint inhibitor-resistant tumor are administered between 1 day and 2 weeks after the administration of the antigen-loaded nanogel.

18. The method according to claim 14, wherein the immune-enhancing agent is TLR (Toll-like receptor) agonists selected from the group consisting of CpG oligoDNA or poly-IC RNA.

19. The method according to claim 2, wherein the immune-enhancing agent is TLR (Toll-like receptor) agonists selected from the group consisting of CpG oligoDNA or poly-IC RNA.

20. The method according to claim 10, wherein the long peptide antigen or a protein antigen is composed of 23 to 80 amino acid residues.

\* \* \* \* \*